(12) United States Patent
Westermann et al.

(10) Patent No.: US 11,071,487 B2
(45) Date of Patent: Jul. 27, 2021

(54) EEG MONITOR WITH A HOUSING INDIVIDUALLY FITTED TO A PERSON

(71) Applicant: T&W Engineering A/S, Lynge (DK)

(72) Inventors: Soren Erik Westermann, Lynge (DK); Rasmus Stig Jensen, Lyngby (DK)

(73) Assignee: T&W Engineering A/S, Lynge (DK)

( * ) Notice: Subject to any disclaimer, the term of this patent is extended or adjusted under 35 U.S.C. 154(b) by 229 days.

(21) Appl. No.: 15/800,615

(22) Filed: Nov. 1, 2017

(65) Prior Publication Data

US 2018/0055398 A1 Mar. 1, 2018

Related U.S. Application Data

(63) Continuation of application No. PCT/EP2015/059643, filed on May 4, 2015.

(51) Int. Cl.
*A61B 5/291* (2021.01)
*A61B 5/00* (2006.01)
*A61B 5/374* (2021.01)

(52) U.S. Cl.
CPC ............ *A61B 5/291* (2021.01); *A61B 5/0031* (2013.01); *A61B 5/6815* (2013.01); *A61B 5/0006* (2013.01); *A61B 5/374* (2021.01); *A61B 2562/12* (2013.01)

(58) Field of Classification Search
CPC ....... A61B 5/0478; A61B 5/00; A61B 5/0031; A61B 5/6815; A61B 5/048; A61B 2562/12; A61B 5/0006; A61B 5/291; A61B 5/374

See application file for complete search history.

(56) References Cited

U.S. PATENT DOCUMENTS

| 5,864,640 | A | 1/1999 | Miramonti et al. |
| 6,101,259 | A | 8/2000 | Rapps |
| 6,965,690 | B2 | 11/2005 | Matsumoto |
| 7,729,774 | B1 | 6/2010 | Lynch et al. |
| 2003/0155173 | A1 | 8/2003 | Widmer et al. |
| 2005/0150499 | A1* | 7/2005 | Bordewick ....... A61M 16/0666 128/206.27 |
| 2009/0074221 | A1* | 3/2009 | Westermann .......... H04R 25/65 381/327 |

(Continued)

FOREIGN PATENT DOCUMENTS

| CN | 102549853 A | 7/2012 |
| CN | 103416077 A | 11/2013 |

(Continued)

OTHER PUBLICATIONS

Communication dated Mar. 27, 2019, from the Canadian Intellectual Property Office in corresponding Application No. 2,983,197.

(Continued)

*Primary Examiner* — Eric J Messersmith
(74) *Attorney, Agent, or Firm* — Sughrue Mion, PLLC (57) ABSTRACT

An EEG monitor adapted for being arranged in the ear region of a person and including a housing (11) holding a power supply (25) and an EEG signal processor (10). The EEG monitor (5) includes an EEG sensing part (12) having EEG electrodes (17). The EEG sensing part (12) is adapted for arrangement subcutaneously at the scalp or in the ear canal of the person, and the housing (11) is individually shaped to fit behind or above an ear of the person and into the cleft between a pinna and the skull of the person.

7 Claims, 5 Drawing Sheets

(56) References Cited

U.S. PATENT DOCUMENTS

| | | | |
|---|---|---|---|
| 2012/0235820 A1* | 9/2012 | Kidmose | A61B 5/0476 340/573.1 |
| 2014/0321682 A1 | 10/2014 | Kofod-Hansen et al. | |
| 2015/0280483 A1* | 10/2015 | Golko | H02J 50/90 320/108 |
| 2017/0112408 A1* | 4/2017 | Durand | A61B 5/0478 |

FOREIGN PATENT DOCUMENTS

| | | | |
|---|---|---|---|
| WO | 03/034783 | A2 | 4/2003 |
| WO | 2006/066577 | A1 | 6/2006 |
| WO | 2011/038767 | A1 | 4/2011 |
| WO | 2011/066852 | A1 | 6/2011 |
| WO | 2011/091856 | A1 | 8/2011 |
| WO | 2012/095171 | A1 | 7/2012 |
| WO | 2012/104142 | A1 | 8/2012 |

OTHER PUBLICATIONS

Communication dated May 20, 2019, from the Korean Intellectual Property Office in corresponding Application No. 10-2017-7034845.
International Search Report for PCT/EP2015/059643 dated Dec. 14, 2015.
Communication dated Nov. 13, 2018 issued by the Japanese Patent Office in counterpart application No. 2017-557188.
Communication dated Nov. 22, 2019, from the State Intellectual Property Office of the P.R. of China in Application No. 201580079579.8.

* cited by examiner

EEG MONITOR WITH A HOUSING INDIVIDUALLY FITTED TO A PERSON

This application is a continuation application of PCT Application No. PCT/EP/2015/059643, filed May 4, 2015, the entire contents of all of which are incorporated herein by reference.

BACKGROUND OF THE INVENTION

The present invention relates to an EEG monitor. The invention, more specifically, relates to an EEG monitor adapted for being arranged in the ear region of a person and comprising a housing which is holding a power supply and an EEG signal processor.

The EEG monitor further comprises an EEG sensing part with EEG electrodes. This EEG sensing part is adapted for arrangement subcutaneously at the scalp or in the ear canal or partly in the ear canal of the person.

EEG is the commonly used abbreviation for Electro Encephalography, which is a method of electrically monitoring brain activity of a person. In recent years, EEG monitoring systems, which may be carried or worn continuously by a person to be monitored, have been devised. One goal is to have personal wearable EEG monitors which are small enough to be carried without causing more inconvenience than glasses or a modern hearing aid, even when carried over an extended interval of time, e.g. several months or years.

Such EEG monitors may be applied for purposes of surveillance of a condition of the person and for providing some kind of alarm or information in case predetermined conditions are met. The monitor may also be applied for collection of data for further analysis, e.g. for diagnostic purposes or for research use. An example of an application is for surveillance of persons having diabetes, where blood sugar levels are monitored in order to warn against hypoglycemic attacks caused by low blood sugar levels. Hypoglycemic attacks may lead to unconsciousness and even death. A system for such surveillance of the persons EEG and analysis of the EEG signal in order to predict an imminent hypoglycemic attack is disclosed in WO-A-2006/066577.

EEG monitors typically comprise an electrode part, which is either subcutaneously implanted or it is arranged externally with electrodes on the skin surface or in the ear canal. In case the electrode part is implanted, this implant may be connected through an inductive link to an external processor part comprising a power supply. An example of this is described in WO-A-2006/066577.

This external part of an EEG monitor can preferably be arranged at an ear of the person to be monitored.

An EEG monitor is often supposed to be carried by a person all day, and often even through the night. This means that an optimal shape of the monitor to fit behind or above the ear of the person is important for the convenience of the person, and in order to avoid any skin related problems such as skin irritation at the place where the monitor is arranged.

The monitor will often also need to be carried during sleeping, physical exercise and sport activity. Also here it is important that the monitor has a good fit behind the ear, both to be convenient for the person to carry and also to minimise the risk of losing the monitor, and to minimise the risk that the monitor is displaced and will no longer function.

In the situation that the EEG monitor comprises an implantable sensing part with electrodes and an external part connected through an inductive link, it is important that the external part stays at the same placement in order for the inductive link to function optimally.

SUMMARY OF THE INVENTION

A solution to these challenges has been found in an EEG monitor where the housing is individually shaped to fit behind or above an ear of said person and into the cleft between a pinna and the skull of said person.

One advantage of this solution is that the housing can be easily arranged into one pre-selected position, from which it will not easily move away during use.

In an embodiment the EEG monitor housing has been manufactured by a 3D printing technology based on a scanning of the person's ear region. It may be the entire housing or main parts of the housing which is manufactured by 3D printing. This scanning may be optically based, e.g. by a 3D laser scanner, which are commercially available, or by image processing of photographs or video. The scanning can be made directly or of an imprint of the site where the housing is to be placed. The 3D printing based on scanning has the advantage that the housing can be adapted individually, even in the smallest details. At the same time this technology will be both cost and time saving.

In a further embodiment the EEG sensing part of the EEG monitor is adapted for subcutaneous implantation behind the ear of the person to carry the EEG monitor. The EEG monitor comprises an inductive link between the EEG sensing part and the EEG signal processor in the housing. Having the EEG sensing part arranged subcutaneously facilitates that the EEG signal at the electrodes will be relatively stronger, and that the level of noise is reduced. The inductive link provides for a stable and reliable transfer of data to the EEG signal processing part. The inductive link preferably comprises a first coil in the EEG sensing part, and a second coil in the housing.

In a further embodiment the housing of the EEG monitor is shaped, and the second coil is arranged in said housing, such that when positioned behind the ear of the person the first and the second coils are aligned. Alignment of the two coils, e.g. such that their axes coincide or approximately coincide, means that the transfer of data is reliable, and that any transfer of energy is efficient.

In a further embodiment the housing of the EEG monitor is provided with a recessed area, situated at the area of the housing, which is adapted to abut the skin at the spot where the EEG sensing part is implanted below the skin. This means that the positioning of the housing will be more stable. It also means that any pressure asserted on the housing will not transform into a pressure on the implanted part. This may be relevant e.g. when wearing the monitor during sleeping, where the person should be able to lie on the side where the EEG monitor is arranged.

In a further embodiment of the EEG monitor at least a part of a surface of the housing that is adapted to abut the skin of the person during use is provided with a surface texture allowing for air circulation between said housing and said skin. This may be particularly advantageous in case the housing is individually fitted and therefore adapted for being placed in close contact with a relatively larger area of the skin. Some level of air circulation reduces the risk of skin irritation. One embodiment of this may be that the surface texture comprises a number of grooves.

In a further embodiment of the EEG monitor the housing is connectable with a fastening device for securing the housing in the correct position during sport or when sleeping. This fastening device may be in the form of a relatively stiff wire or tube which also may be used for providing sound, e.g. in the form of messages or alarms, to the ear canal of the person wearing the monitor.

In a further embodiment of the EEG monitor the sensing part is adapted to be arranged in the ear canal of the person, and the shape of the sensing part is fitted to the shape of the ear canal, this fitting is based on a scanning of the ear canal. This will ensure that the sensing part fits in the ear canal, and that the electrodes of the sensing part therefore can obtain a good and stable skin contact, which is important for the detection of an EEG signal.

In a second aspect the invention is directed at a method for providing an individually fitted housing for an EEG monitor. The EEG monitor comprises a sensing part external to the housing and a processing part in the housing. The method comprises the steps:
  determining the preferred position of said housing,
  scanning the contour of this preferred position,
  establishing a computerized model of said housing from this scanned contour,
  designing an individually fitted housing based on this model, and
  printing said housing.

This method provides for a fast and accurate way of manufacturing an individually fitted housing. The determination of the preferred position may take a possible implanted part, which may form a small bulge, into account. Scanning of the contour can be done by a number of photographs from different angles, or by laser scanning, or by making an imprint and scanning the imprint. The printing can be a three dimensional (3D) printing technique.

In an embodiment of this method where the sensing part is implanted e.g. subcutaneous, the method comprises a step of placing a second coil in the housing such that this second coil, when the EEG monitor is in normal use, will be aligned with a first coil of the implanted sensing part. With this arrangement an inductive link is formed. The two coils are aligned when there is a good inductive coupling between them, e.g. when their centers are placed on the same axis or approximately on the same axis. A good inductive coupling is important for the efficiency in power and data transfer.

In a further embodiment of the method, the sensing part is adapted to be arranged in an ear canal of a person who is to apply the EEG monitor. The method comprises a step wherein the shape of said sensing part is fitted to the shape of the ear canal. This step also involves performing a scanning of the ear canal. Such fitting ensures a good and stable contact between the electrodes and the skin.

BRIEF DESCRIPTION OF THE DRAWINGS

Embodiments of the invention will now be explained in further detail with reference to the figures.

DETAILED DESCRIPTION OF THE INVENTION

Figure 1:
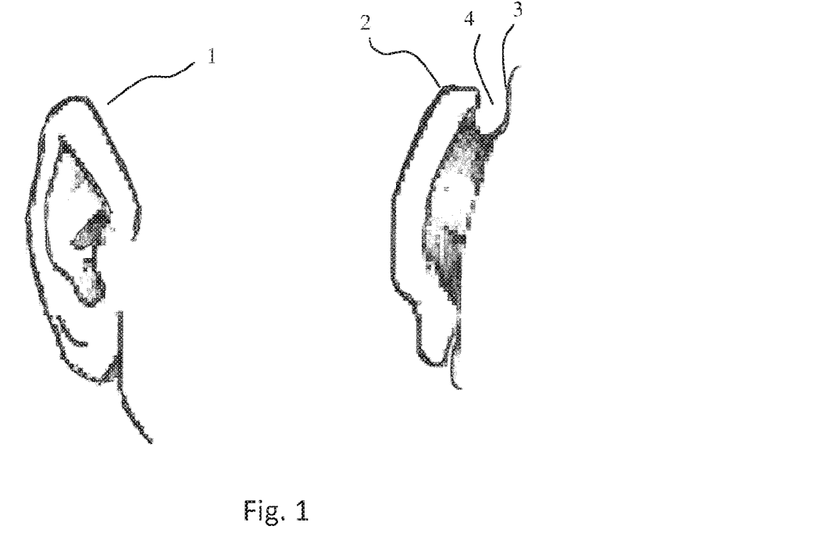
FIG. 1 illustrates a human ear.

FIG. 1 shows an ear 1 of a person, to the left side as seen from the front and to the right side as seen from behind, the front being defined as the side the person is looking towards. FIG. 1 (right side) defines the pinna 2, the skull 3, and the cleft 4 between the pinna 2 and the skull 4.

Figure 2:
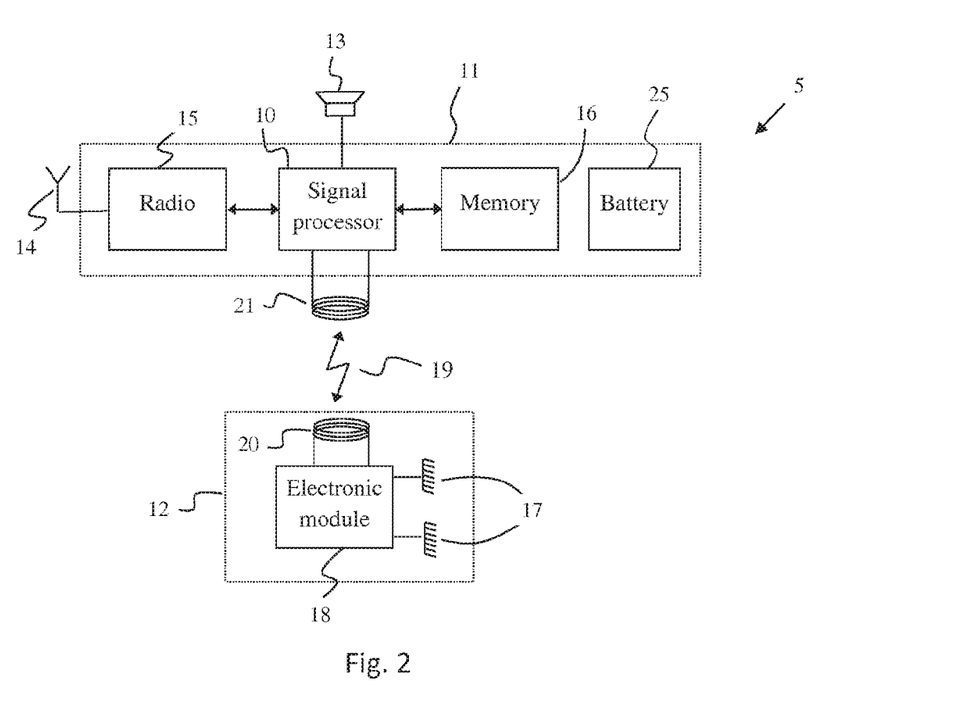
FIG. 2 illustrates an EEG monitor.

FIG. 2 shows an example of an EEG monitor in more details. The EEG monitor 5 comprises an external EEG signal processor part 11 and an implantable EEG sensing part 12. The EEG sensing part 12, suitable for being subcutaneously positioned behind the ear of a person, comprises subcutaneous EEG electrodes 17 connected to an electronic module 18. The number of EEG electrodes is at least two. Often at least three electrodes or more are preferred. The electronic module 18 often comprises an A/D converter (not shown) and a communication controller (not shown), and a voltage regulator (not shown). The electrodes 17 are connected to the A/D converter; the communications controller is connected to a first coil 20 of an inductive link 19.

The EEG signal processor part 11, preferably adapted for being arranged in one housing, comprises a signal processor 10 having a controller (not shown) connected to a second coil 21 of the inductive link 19. The signal processor 10 is further connected to a battery 25 for power supply and to a loudspeaker 13 for providing an acoustic signal, e.g. a notification to the user or, in case the EEG monitor is applied for surveillance of a person e.g. in risk of having hypoglycemia, an alarm to the user in the event that an upcoming onset of hypoglycemia is identified. The EEG signal processor part 11 also comprises a memory 16, e.g. for logging of data, as well as a radio 15 with an antenna 14, for wireless communication with external units.

When in use, the EEG signal processor 11 may be placed behind the ear of a person for whom monitoring of an EEG signal is desired, and in the vicinity of a subcutaneously implantable EEG sensing part 12, which preferably is implanted right below the skin and slightly behind the ear of the user and positioned in such a way that a reliable, electrical EEG signal may be detected by the electrodes 17. The electrodes 17 of the EEG sensing part 12 can be arranged in one wire having the electrodes 17 arranged with contact to the tissue in limited areas along the wire. Such a wire comprising all electrodes associated with respective conductors may facilitate the implantation process.

As an alternative to the implanted sensing part 12 with electrodes, the sensing part could also be arranged non-implanted at the body with external skin surface electrodes. One example of this could be as an earplug arranged in the ear canal with skin surface electrodes detecting an EEG signal from the ear canal earplug sensing part. This earplug based sensing part can be in wired connection with an EEG signal processing part arranged behind the ear.

Figure 3:
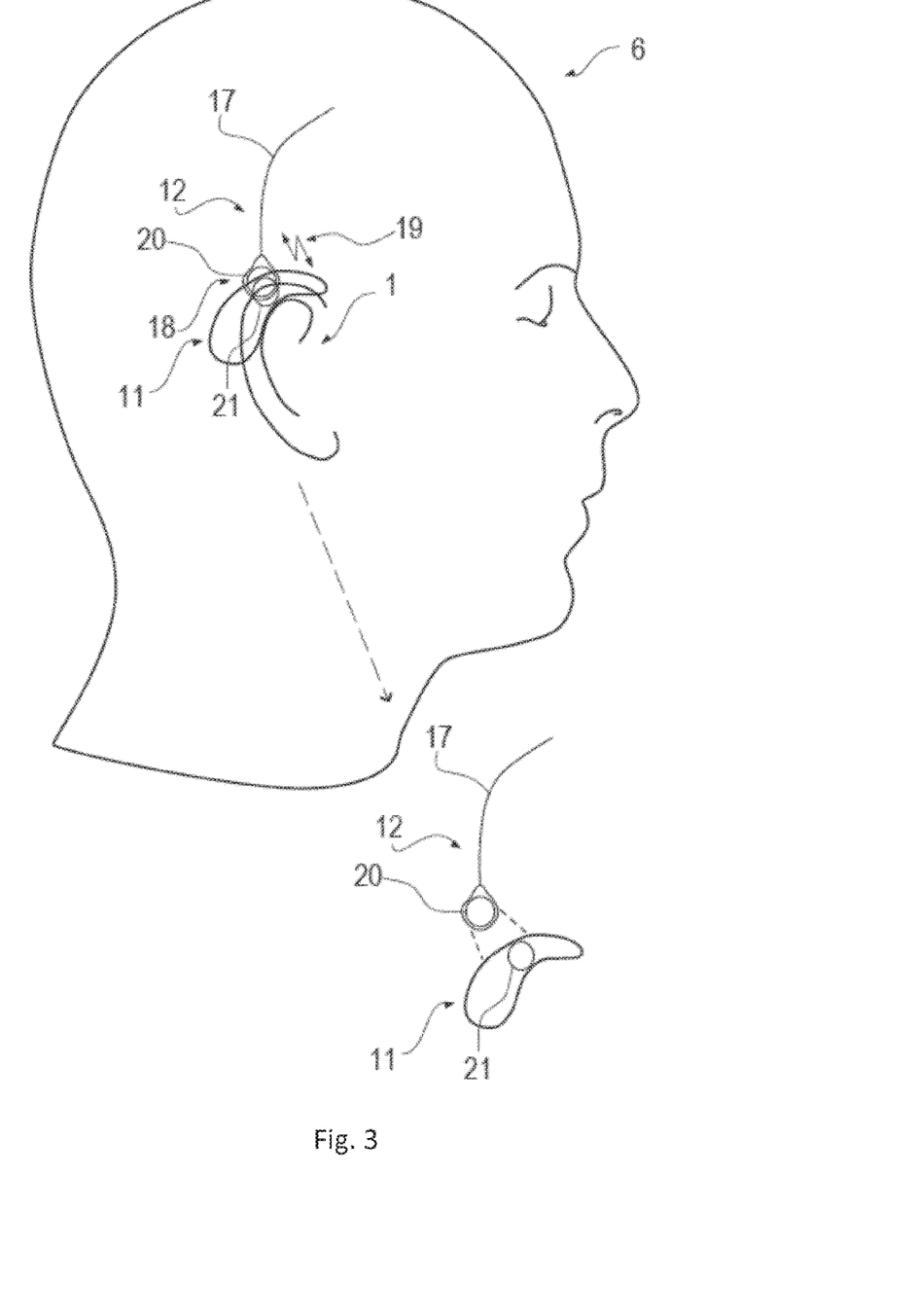
FIG. 3 illustrates an EEG monitor arranged at the head of a person.

FIG. 3 shows the head 6 of a person provided with an EEG monitor 5. The person being monitored is wearing an implantable EEG sensor part 12 having at least two electrodes 17, and a housing comprising the EEG signal processor 11. These two parts 11, 12 are adapted to be in wireless communication through the skin of the person by an inductive link 19. In FIG. 3 the first coil 20 and the second coil 21 are supposed to be arranged such that the two coils 20, 21 have their centers on the same axis. This will render the inductive link as efficient as possible. This is also illustrated at the bottom of FIG. 3, were it is indicated that the housing 11 is arranged such that the second coil 21 is arranged over the first coil 20, which is in the subcutaneously implanted sensing part 12.

The housing comprising the EEG signal processor 11 is arranged at the ear of the person of whom the EEG signal is being monitored. Preferably, the housing is arranged behind the ear as a behind the ear hearing aid. This also facilitates a position as close as possible to the implanted part, which is important for the wireless communication and power transfer through the skin. With the position behind the ear of the housing, means for fixation is also preferable. For this purpose part of a wire or sound tubing also applied for conveying the sound from a hearing aid into the ear canal may be used. This means that this wire or sound tubing should preferably be relatively stiff, i.e. adapted for keeping the original given shape during use. Further to this purpose the wire or the sound tube can also be used for providing a sound alarm or message to the user. In the case of applying a wire, the loudspeaker or receiver could be arranged within or close to the ear canal. In the case of applying a sound tube, the loudspeaker or receiver could be arranged in the housing of the processing unit.

Figure 4:
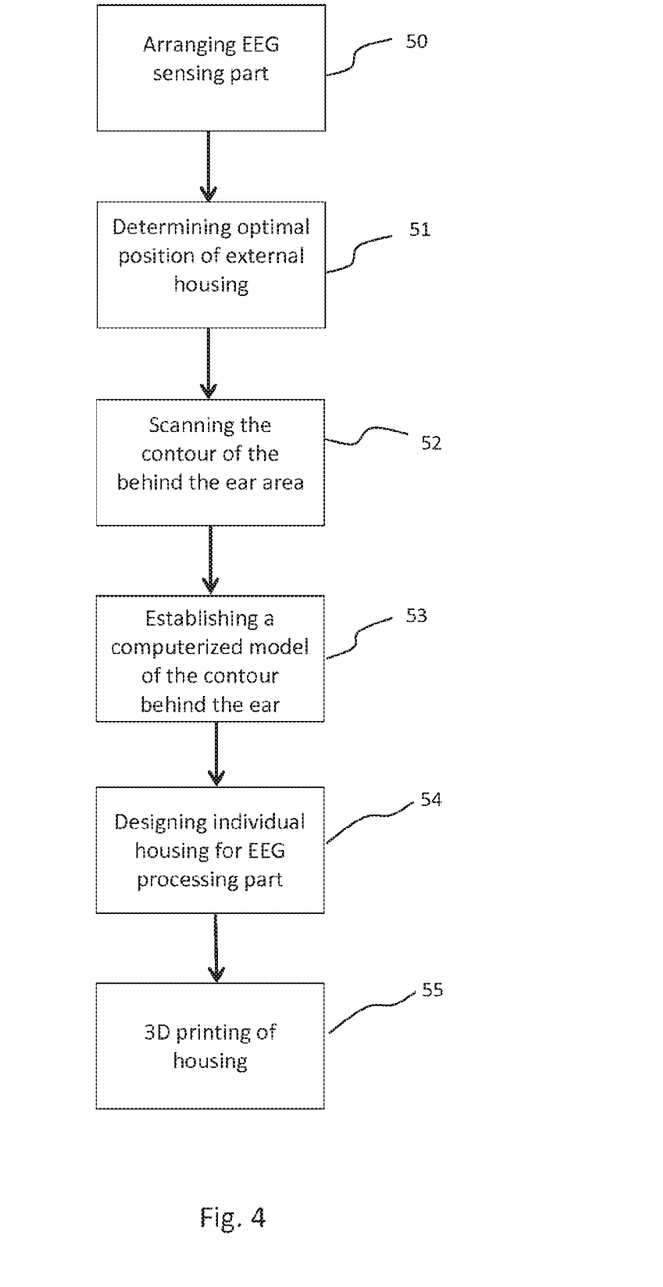
FIG. 4 illustrates a flowchart of a method for providing an individually shaped housing for an EEG monitor.

FIG. 4 shows the method steps which may be performed in order to provide a housing for an EEG monitor which is individually fitted for arrangement behind, or above, the ear in the cleft between the scull and the pinna.

The first step 50 could be the arrangement of the EEG sensing part with the EEG electrodes. This could be the implantation of an implantable EEG sensing part, or the arrangement of an earplug with skin surface electrodes in the ear canal and a connecting cable to the housing comprising the EEG processing part.

It is noted that the implantation of an implantable EEG sensing part or any electrode device is not part of the invention, and any such implantation step is therefore disclaimed.

After arrangement of the EEG sensing part, and maybe after any swelling due to the implantation procedure has vanished, the optimal position of the housing for the processing part of the EEG monitor can be determined, i.e. step 51.

The next step 52 is to scan or record the exact contour of the area behind the ear where the housing is to be arranged, i.e. the cleft between the pinna and the scull where the housing is to be placed.

Digitizing this contour, or mapping this area presupposes some kind of measurements of the area. This could be imaging based on a number of photographs from different angles or on video recording.

U.S. Pat. Nos. 5,864,640 and 6,965,690 B2 illustrates methods for such types of scanning.

Another method for digitizing the contour is to use a laser scanning device, either directly, or by scanning a cast impression made by e.g. a wax or modelling clay material. Commercial 3D scanners may be applied for both situations.

Based on the scanning or photographing of the contour; a computerized model of the contour behind the ear is established (step 53). This model, or the mapping of this contour, could also include information directed on the exact positioning of each part which is to be placed in the housing.

With basis in this computerized model an individual fitted housing for the EEG processing part can be designed (step 54). In this designing process the components to be contained in the housing may be arranged as one pre-assembled block, or they may be arranged individually. The individual arrangement of the components may provide more flexibility in the layout of the housing, but the assembling and handling of the components may also become more time consuming in production.

The last step 55 in FIG. 4 is the 3D printing of the housing. Following this step, the components of the EEG processing part are arranged in the housing, and it is tested that the device functions as intended.

The housing may be provided with a soft outer layer, such as silicone, which could also be manufactured by some 3D printing technique, or by casting the soft outer layer in a 3D printed mold and then arranging it on the housing.

Figure 5:
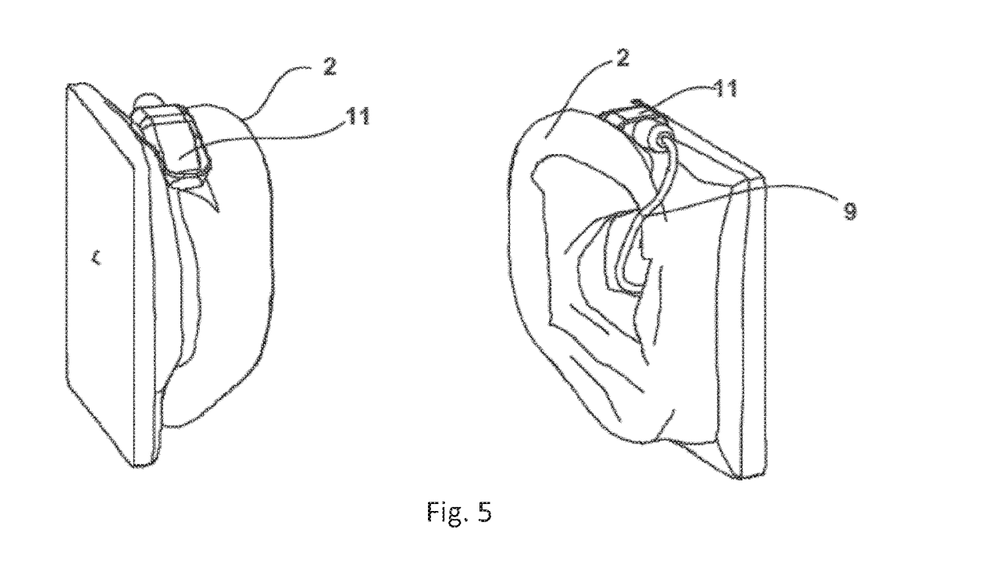
FIG. 5 illustrates an EEG monitor arranged behind a mock-up ear.

FIG. 5 shows a model ear with an individually fitted external part 11 of an EEG monitor arranged slightly above the ear in the cleft between the pinna 2 and the skull of a person. At the left part of FIG. 5, the ear is shown from behind, and at the right part of FIG. 5, the ear is shown from the front. In the right part, a tube or cable 9 is also shown. This may be a sound tube for guiding a sound from a speaker in the external part towards the ear canal of the person wearing the monitor, or it may be a cable with at least two wires for providing an electrical signal to a speaker arranged in or close to the ear canal. This is optional and may have two purposes; one is for providing any sound message or alarm from the EEG monitor to the person, and a second purpose is to function as a fastener, if the cable or tube has sufficient stiffness, and is shaped to assist the external device in staying in the selected position.

Figure 6:
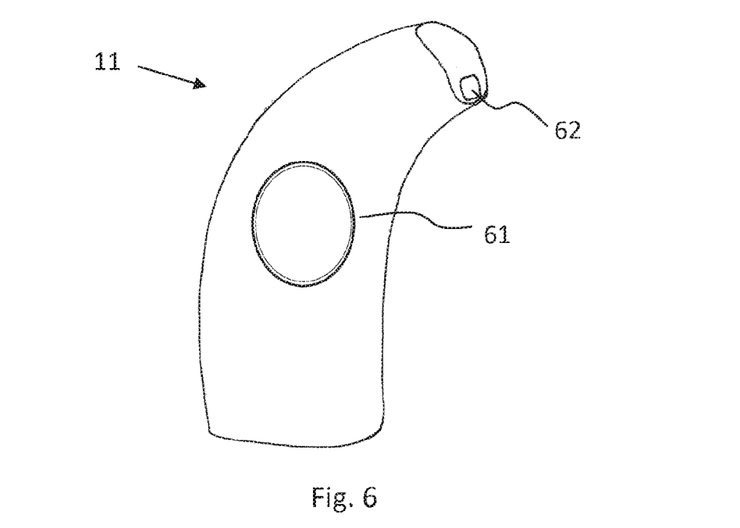
FIG. 6 illustrates the housing of an EEG signal processor part having a recessed area.

The advantage of individually fitting the external part of an EEG monitor with an implanted part is that the housing for the external part, i.e. the signal processor part 11, can be shaped to fit the small bulge on the scull above or behind the ear, which the implanted part may form. This is shown in FIG. 6, where a circular or substantially circular area 61 has been recessed in the individually shaped housing for the signal processor part 11. This recess 61 in the housing is preferably made for encompassing this bulge created by the implanted part. The recess 61 may have whatever shape which will make the housing fit well to the individual person, and the recess area may extend to the edge of the housing.

The opening 62 is for the connection to a cable or sound tube 9, also shown in FIG. 5, for either providing an electrical signal to a speaker or for guiding sound from the signal processor part 11 to the ear canal of the person.

Figure 7:
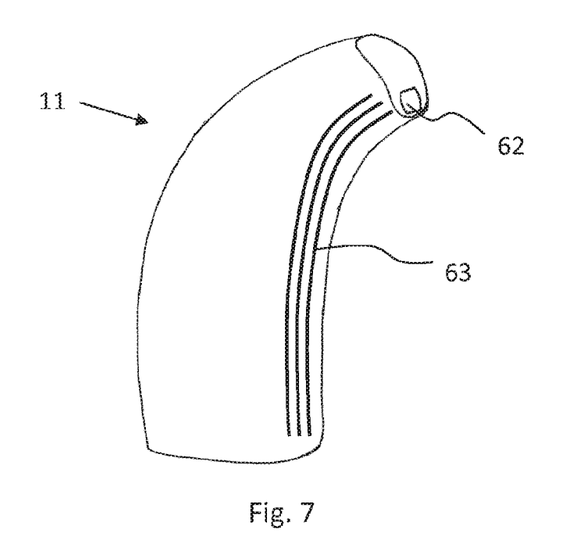
FIG. 7 illustrates an EEG signal processor part having a surface texture allowing for air circulation between the housing and the skin.

FIG. 7 shows that the individually fitted external part 11 may be provided with a surface structure 63 at the parts adapted to be in contact with the skin, which allows for some degree of air ventilation, such that humidity e.g. from perspiration can escape. This surface structure could be a number of grooves as indicated in FIG. 7, each having a sufficient depth such that they will not be blocked by the skin. The grooves may extend along the full length or substantially the full length of the housing.

Parts of the surface of the housing shown in FIG. 6 or 7 may also be provided with one or more electrodes for detecting EEG signal, or for functioning as a reference electrode in the EEG signal detection. Such an electrode could be arranged at an area of the housing surface where there is a close and reliable skin contact.

Since an individually fitted external part of an EEG monitor may have a design and a look which is less smart and fashionable than a standard, not individually shaped, device, the person needing EEG monitoring may be provided with two external parts, one which is individually fitted and therefor stays in the correct position also during sleep and sport, and one which is designed with more focus on visual appearance and design which the person might prefer to use when doing office like work or going to social arrangements etc.

The invention claimed is:

1. An EEG monitor adapted for being arranged in the ear region of a person and comprising a housing holding a power supply and an EEG signal processor, said EEG monitor further comprising an EEG sensing part having EEG electrodes, said EEG sensing part adapted for arrangement subcutaneously at the scalp, wherein said housing is individually shaped by custom fitting to fit behind or above an ear of said person and into the cleft between a pinna and the skull of said person, whereby said housing has external surface characteristics matching contours of at least one of said pinna and skull of said person, wherein:
- said EEG sensing part is adapted for subcutaneous implantation behind the ear of said person;
- said EEG monitor comprises an inductive link between said EEG sensing part and said EEG signal processor in said housing, said inductive link comprising a first coil in said EEG sensing part and a second coil in said housing; and
- said housing is shaped and said second coil is arranged in said housing such that when positioned behind the ear of said person said first and said second coils are aligned, and wherein said housing is provided with a recessed area, situated at the area of the housing adapted to abut the skin at the spot where the EEG sensing part is implanted below the skin.

2. The EEG monitor according to claim 1, wherein said housing has been fully or partly manufactured by a 3D printing technology based on a scanning of said person's ear region or on a scanning of an imprint of said person's ear region.

3. The EEG monitor according to claim 1, wherein at least a part of a surface of said housing adapted to abut the skin of said person when in use is provided with a surface texture allowing for air circulation between said housing and said skin.

4. The EEG monitor according to claim 3, wherein said surface texture comprises a number of grooves.

5. The EEG monitor according to claim 1, wherein said monitor includes a fastening device for securing the housing in the correct position during sport or when sleeping.

6. The EEG monitor according to claim 1, wherein at least a part of a surface of said housing adapted to abut the skin of said person when in use is provided with a surface texture allowing for air circulation between said housing and said skin.

7. A method for providing a housing that is individually fitted to a user of an EEG monitor, said EEG monitor comprising an implanted sensing part external to said housing, a processing part in said housing, said implanted sensing part having a first coil for inductively coupling to a second coil in said housing, said method comprising the steps of
- determining the preferred position of said housing on said user, scanning the contour of said user at this preferred position,
- establishing a computerized model of said housing from this scanned contour,
- designing an individually fitted housing based on this model, said housing being configured to accommodate said second coil such that, when the EEG monitor is in use, the second coil will be aligned with said first coil, and wherein said housing is provided with a recessed area, situated at the area of the housing adapted to abut the skin at a location where the implanted sensing part is below the skin, and
- printing said housing.

* * * * *